US006693210B2

(12) United States Patent
Miyaura

(10) Patent No.: US 6,693,210 B2
(45) Date of Patent: Feb. 17, 2004

(54) TRIPHENYLPHOSPHINE DERIVATIVE, PRODUCTION PROCESS THEREFOR, PALLADIUM COMPLEX THEREOF, AND PROCESS FOR PRODUCING BIARYL DERIVATIVE

(75) Inventor: Norio Miyaura, Hokkaido (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/221,678

(22) PCT Filed: Mar. 14, 2001

(86) PCT No.: PCT/JP01/02011

§ 371 (c)(1), (2), (4) Date: Sep. 13, 2002

(87) PCT Pub. No.: WO01/68657

PCT Pub. Date: Sep. 20, 2001

(65) Prior Publication Data

US 2003/0065208 A1 Apr. 3, 2003

(30) Foreign Application Priority Data

Mar. 14, 2000 (JP) ........................................ 2000-070711

(51) Int. Cl.$^7$ ................................................. C07F 9/50
(52) U.S. Cl. ........................... 556/21; 564/15; 560/129; 560/182; 568/13
(58) Field of Search ............................ 564/15; 560/129, 560/182; 568/13, 17; 556/13, 19, 20, 21; 549/429, 29; 546/1

(56) References Cited

U.S. PATENT DOCUMENTS

2002/0012631 A1 * 1/2002 Liu ........................... 424/9.36

FOREIGN PATENT DOCUMENTS

| JP | 8-59514 | 3/1996 |
| WO | 98/28315 | 7/1998 |
| WO | 98/45265 | 10/1998 |

OTHER PUBLICATIONS

Masato Ueda et al.: "A palladium–catalyzed biaryl coupling of arylboronic acids in aqueous media using a gluconamide–substituted triphenylphosphine (GLCAphos) ligand", SYNLETT, No. 6, pp. 856–858, 2000.

N. Miyaura et al.: "The palladium–catalyzed cross–coupling reaction of phenylboronic acid with haloarenes in the presence of bases" Synthetic Communications, vol. 11, No. 7, pp. 513–519, 1981.

Albert L. Casalnuovo et al.: "Palladium–catalyzed alkylations in aqueous media" J. Am. Chem. Soc., vol. 112, pp. 4324–4330, 1990.

Matthias Beller et al.: "Carbohydrate–substituted triarylphosphanes—a new class of ligands for two–phase catalysis" Angew. Chem. Int. Ed. Engl., vol. 36, No. 7, pp. 772–774, 1997.

* cited by examiner

Primary Examiner—Jean F. Vollano
(74) Attorney, Agent, or Firm—Oblon, Spivak, McClelland, Maier & Neustadt, P.C.

(57) ABSTRACT

Provided are a novel triphenyl phosphine derivative synthesized from a triphenylphosphine and a hydroxy-containing lactone; a palladium and a nickel complexes comprising the derivative as a ligand; and a process for preparing a biaryl derivative using the complex as a catalyst. A product can be easily separated from a catalyst or a phosphorus compound, and biaryl derivative can be synthesized in a higher yield, by using the complex of the present invention as a catalyst.

18 Claims, No Drawings

TRIPHENYLPHOSPHINE DERIVATIVE, PRODUCTION PROCESS THEREFOR, PALLADIUM COMPLEX THEREOF, AND PROCESS FOR PRODUCING BIARYL DERIVATIVE

TECHNICAL FIELD

This invention relates to a process for preparing a biaryl derivative useful as an intermediate for a medical or agricultural agent; a novel water-soluble ligand complex useful as a catalyst for the preparation process; as well as a novel triphenylphosphine derivative with which the complex can be prepared and a preparation process therefor.

BACKGROUND ART

Conventionally, a biaryl derivative has been typically prepared according to a process described in N. Miyaura, A. Suzuki, Synth. Commun., 11, 513 (1981), which has been extensively utilized not only in medical/agricultural applications but also organic synthesis.

The process, however, has drawbacks that a product is contaminated with palladium and phosphorous compounds requiring acid decomposition of a catalyst and then common purification such as column chromatography and recrystallization for removing them. Thus, application to a larger industrial scale requires especially easier separation of the product from a catalyst and a phosphorous compound and reduction of the amount of the catalyst.

For solving the problem of separation of the product from the catalyst, there have been known processes where a catalyst used is solubilized in water and at the end of the reaction a desired biaryl derivative is extracted with an organic layer, e.g., (A) synthesis of a biaryl derivative using a water-soluble palladium complex derived from a water-soluble phosphine ligand such as triphenylphosphino-3,3,3-trisulfonate trisodium salt (TPPTS) described in JP-A 8-59514; (B) synthesis of a biaryl derivative using a water-soluble palladium complex derived from a water-soluble phosphine ligand such as triphenylphosphino-3-sulfonate sodium salt (TPPMS) described in A. Casalnuovo, J. Am. Chem. Soc. 112, 4324 (1990), (C) using a water-soluble phosphine ligand prepared from diphenyl-4-hydroxyphenyl phosphine and a hexose to provide a water-soluble palladium complex, which is then used as a catalyst for preparing a biaryl derivative described in M. Beller, Angew. Chem. Int. Ed. Engl., 36, 772 (1997).

The process in (A) has drawbacks such as a longer reaction period and a lower yield because of a two-phase reaction. For the process in (B), an yield in a single-phase reaction is lower. The process in (C) has drawbacks such as an extremely lower yield of the ligand as the starting material for the catalyst.

DISCLOSURE OF THE INVENTION

There has been desired to develop a novel water-soluble phosphine ligand and its palladium or nickel complex which can be conveniently prepared in an improved yield, whereby in a reaction of, for example, an aryl halide with an arylboronic acid for preparing a biaryl derivative, the biaryl derivative as a product can be provided in a higher yield and the product can be easily separated from a catalyst and a phosphorous compound. Thus, objectives of this invention are to provide such a water-soluble phosphine ligand and a preparation process therefor, to provide such a complex and to provide a convenient process for preparing a biaryl derivative in a higher yield.

The inventors have intensely applied themselves to the above objectives and have finally developed a completely novel triphenylphosphine derivative and a palladium and a nickel complexes comprising the derivative as a ligand, and have established a very useful preparation process having the following features: (1) it can be used not only in an organic phase but also in an aqueous phase or a two-phase reaction system of an aqueous phase and an organic phase, (2) a catalyst and a phosphorous compound can be easily removed by post-treatment after the reaction such as water washing, and contamination with the complex or the phosphorous compound can be eliminated and (3) the biaryl derivative can be provided in a good yield using a very small amount of the catalyst.

Specifically, in the first aspect, this invention provides a triphenyl phosphine derivative represented by formula (I):

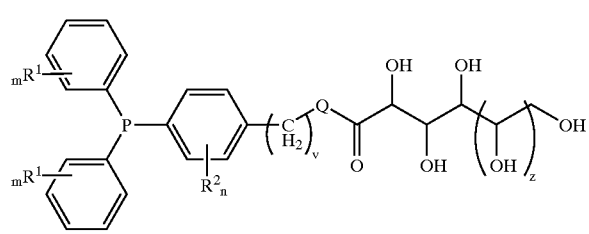

(I)

[in the formula (I), $R^1$ and $R^2$, which may be the same or different, represent hydrogen atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms, fluoroalkyl with 1 to 6 carbon atoms or aminoalkyl with 1 to 3 carbon atoms; m and n independently represent 1 or 2; v represents an integer of 0 to 3; z represents 1 or 2; and Q represents oxygen atom, sulfur atom or —NR— where R represents alkyl with 1 to 6 carbon atoms or hydrogen atom.]

In the second aspect, this invention provides the triphenyl phosphine derivative according to the first aspect of this invention represented by formula (II):

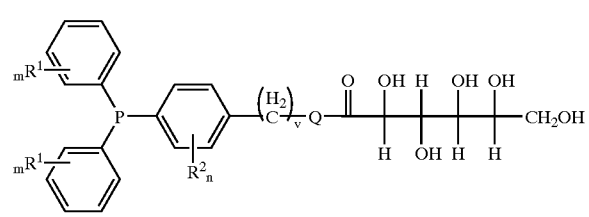

(II)

[in the formula (II), $R^1$ and $R^2$, which may be the same or different, represent hydrogen atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms, fluoroalkyl with 1 to 6 carbon atoms or aminoalkyl with 1 to 3 carbon atoms; m and n independently represent 1 or 2; v represents an integer of 0 to 3; and Q represents oxygen atom, sulfur atom or —NR— where R represents alkyl with 1 to 6 carbon atoms or hydrogen atom.]

In the third aspect, this invention provides the triphenyl phosphine derivative according to the second aspect of this invention wherein in the formula (II), $R^1$ and $R^2$ represent hydrogen; m, n and v represent 1; and Q represents —NR— where R represents alkyl or hydrogen.

In the fourth aspect, this invention provides a process for preparing the triphenyl phosphine derivative according to the first aspect of this invention by reacting a hydroxy-containing lactone with the compound represented by formula (III):

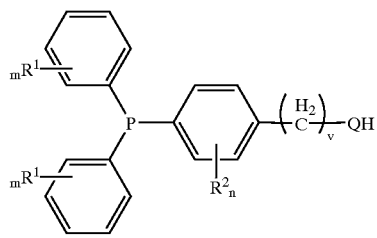

(III)

[in the formula (III), $R^1$ and $R^2$, which may be the same or different, represent hydrogen atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms, fluoroalkyl with 1 to 6 carbon atoms or aminoalkyl with 1 to 3 carbon atoms; m and n independently represent 1 or 2; v represents an integer of 0 to 3; and Q represents oxygen atom, sulfur atom or —NR— where R represents alkyl with 1 to 6 carbon atoms or hydrogen atom.]

In the fifth aspect, this invention provides the process according to the fourth aspect of this invention wherein the hydroxy-containing lactone is δ-gluconolactone. Using this process, the triphenylphosphine derivative according to the third aspect of this invention can be prepared.

In the sixth aspect, this invention provides a phosphine ligand-palladium complex prepared from the triphenylphosphine derivative according to the first aspect of this invention and at least one palladium compound selected from the group consisting of palladium benzylideneacetones, palladium acetylacetonates, nitrile palladium halides, olefin palladium halides, palladium halides and palladium carboxylates.

In the seventh aspect, this invention provides a phosphine ligand-palladium complex prepared from the triphenylphosphine derivative according to the second aspect of this invention and at least one palladium compound selected from the group consisting of palladium benzylideneacetones, palladium acetylacetonates, nitrile palladium halides, olefin palladium halides, palladium halides and palladium carboxylates.

In the eighth aspect, this invention provides a phosphine ligand-palladium complex prepared from the triphenylphosphine derivative according to the third aspect of this invention and at least one palladium compound selected from the group consisting of palladium benzylideneacetones, palladium acetylacetonates, nitrile palladium halides, olefin palladium halides, palladium halides and palladium carboxylates.

In the ninth aspect, this invention provides a phosphine ligand-palladium complex prepared from the triphenylphosphine derivative according to the first aspect of this invention and at least one palladium compound selected from the group consisting of bis(benzylidene)acetone palladium, palladium bisacetylacetonate, dichlorobisacetonitrile palladium, dichlorobisbenzonitrile palladium, dichloro(1,5-cyclooctadiene)palladium, bis(1,5-cyclooctadiene) palladium, tris(dibenzylideneacetone)dipalladium, palladium chloride and palladium acetate.

In the tenth aspect, this invention provides a phosphine ligand-palladium complex prepared from the triphenylphosphine derivative according to the second aspect of this invention and at least one palladium compound selected from the group consisting of bis(benzylidene)acetone palladium, palladium bisacetylacetonate, dichlorobisacetonitrile palladium, dichlorobisbenzonitrile palladium, dichloro(1,5-cyclooctadiene)palladium, bis(1,5-cyclooctadiene)palladium, tris(dibenzylideneacetone) dipalladium, palladium chloride and palladium acetate.

In the eleventh aspect, this invention provides a phosphine ligand-palladium complex prepared from the triphenylphosphine derivative according to the third aspect of this invention and at least one palladium compound selected from the group consisting of bis(benzylidene)acetone palladium, palladium bisacetylacetonate, dichlorobisacetonitrile palladium, dichlorobisbenzonitrile palladium, dichloro(1,5-cyclooctadiene)palladium, bis(1,5-cyclooctadiene)palladium, tris(dibenzylideneacetone) dipalladium, palladium chloride and palladium acetate.

In the twelfth aspect, this invention provides a phosphine ligand-palladium complex prepared from the triphenylphosphine derivative according to the second aspect of this invention and dichloro(1,5-cyclooctadiene) palladium.

In the thirteenth aspect, this invention provides a phosphine ligand-palladium complex prepared from the triphenylphosphine derivative according to the third aspect of this invention and dichloro(1,5-cyclooctadiene) palladium.

In the fourteenth aspect, this invention provide a phosphine ligand-nickel complex prepared from the triphenylphosphine derivative according to the second aspect of this invention and at least one nickel salt selected from the group consisting of nickel halides, nickel nitrates, nickel sulfates, nickel organocarboxylates, nickel-acetylacetonate complex salts and nickel hydroxide.

In the fifteenth aspect, this invention provide a phosphine ligand-nickel complex prepared from the triphenylphosphine derivative according to the third aspect of this invention and at least one nickel salt selected from the group consisting of nickel halides, nickel nitrates, nickel sulfates, nickel organocarboxylates, nickel-acetylacetonate complex salts and nickel hydroxide.

In the sixteenth aspect, this invention provides a process for preparing a biaryl derivative represented by formula (VII) by reacting an aryl halide derivative or aryl sulfonyl derivative represented by formula (IV) with an arylboronic acid, its derivative or an arylboronic anhydride represented by formula (V) or (VI):

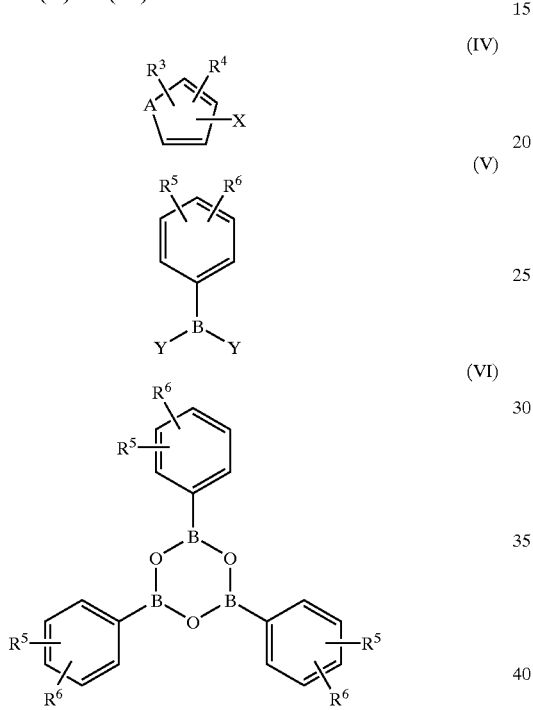

[in the formula (IV), (V) and (VI), A represents S, O, HC=CH or N=CH; $R^3$, $R^4$, $R^5$ and $R^6$, which may be the same or different, represent hydrogen atom, chlorine atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms or fluoroalkyl with 1 to 6 carbon atoms; X represents chlorine, bromine, iodine, mesylate or arenesulfonate; Y represents hydroxy, alkoxy with 1 to 6 carbon atoms, phenoxy optionally having alkyl with 1 to 6 carbon atoms or cyclohexyloxy; or two Ys are combined together to form a group represented by formula a, b or c:

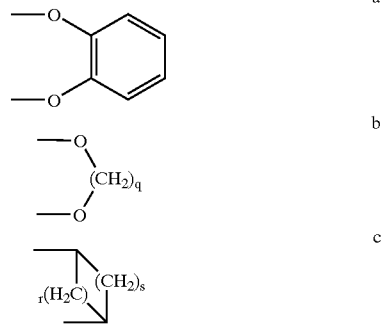

wherein q represents 1, 2, 3 or 4; and r and s independently represent 2, 3, 4 or 5], using the phosphine ligand-palladium complex according to the sixth aspect of this invention as a catalyst, in water, an organic solvent or a mixture of an organic solvent and water, in the presence of a base:

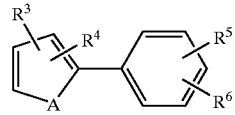

[in the formula (VII), A, $R^3$, $R^4$, $R^5$ and $R^6$ are as defined in the formulas (IV), (V) and (VI).]

In the seventeenth aspect, this invention provides a process for preparing a biaryl derivative according to the sixteenth aspect of this invention wherein the catalyst is the phosphine ligand-palladium complex according to the seventh aspect of this invention.

In the eighteenth aspect, this invention provides a process for preparing a biaryl derivative according to the sixteenth aspect of this invention wherein the catalyst is the phosphine ligand-palladium complex according to the eighth aspect of this invention.

In the nineteenth aspect, this invention provides a process for preparing a biaryl derivative according to the sixteenth aspect of this invention wherein the catalyst is the phosphine ligand-palladium complex according to the ninth aspect of this invention.

In the twentieth aspect, this invention provides a process for preparing a biaryl derivative according to the sixteenth aspect of this invention wherein the catalyst is the phosphine ligand-palladium complex according to the tenth aspect of this invention.

In the twenty-first aspect, this invention provides a process for preparing a biaryl derivative according to the sixteenth aspect of this invention wherein the catalyst is the phosphine ligand-palladium complex according to the eleventh aspect of this invention.

In the twenty-second aspect, this invention provides a process for preparing a biaryl derivative according to the sixteenth aspect of this invention wherein the catalyst is the phosphine ligand-palladium complex according to the twelfth aspect of this invention.

In the twenty-third aspect, this invention provides a process for preparing a biaryl derivative according to the sixteenth aspect of this invention wherein the catalyst is the phosphine ligand-palladium complex according to the thirteenth aspect of this invention.

In the twenty-fourth aspect, this invention provides a process for preparing a biaryl derivative according to the sixteenth aspect of this invention wherein the catalyst is the phosphine ligand-nickel complex according to the fourteenth aspect of this invention.

In the twenty-fifth aspect, this invention provides a process for preparing a biaryl derivative according to the sixteenth aspect of this invention wherein the catalyst is the phosphine ligand-nickel complex according to the fifteenth aspect.

BEST MODE FOR CARRYING OUT THE INVENTION

Preferred embodiments of this invention will be described.

A novel triphenylphosphine derivative of this invention is represented by formula (I):

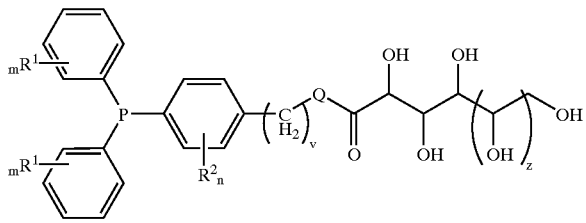

(I)

[in the formula (I), $R^1$ and $R^2$, which may be the same or different, represent hydrogen atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms, fluoroalkyl with 1 to 6 carbon atoms or aminoalkyl with 1 to 3 carbon atoms; m and n independently represent 1 or 2; v represents an integer of 0 to 3; z represents 1 or 2; and Q represents oxygen atom, sulfur atom or —NR— where R represents alkyl with 1 to 6 carbon atoms or hydrogen atom.]

Another novel triphenylphosphine derivative of this invention is represented by formula (II):

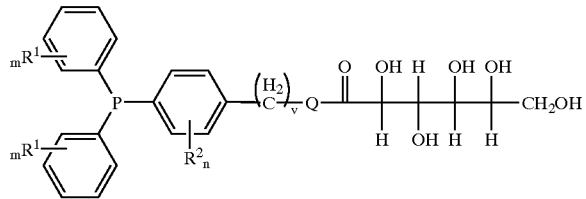

(II)

[in the formula (II), $R^1$ and $R^2$, which may be the same or different, represent hydrogen atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms, fluoroalkyl with 1 to 6 carbon atoms or aminoalkyl with 1 to 3 carbon atoms; m and n independently represent 1 or 2; v represents an integer of 0 to 3; and Q represents oxygen atom, sulfur atom or —NR— where R represents alkyl with 1 to 6 carbon atoms or hydrogen atom.]

Substituents on the triphenylphosphine derivatives represented by the formulas (I) and (II) will be described with reference to specific examples.

Examples of alkyl with 1 to 6 carbon atoms include methyl, ethyl, n-propyl, iso-propyl, n-butyl, iso-butyl, sec-butyl, tert-butyl, n-pentyl, iso-pentyl, sec-pentyl, neopentyl, 1-methylbutyl, 1,2-dimethylpropyl, n-hexyl, 1-methylpentyl and 2-ethylbutyl.

Examples of alkoxy with 1 to 6 carbon atoms include methoxy, ethoxy, n-propoxy, iso-propoxy, n-butoxy, iso-butoxy, sec-butoxy, tert-butoxy, n-pentyloxy, iso-pentyloxy, sec-pentyloxy, neopentyloxy, 1-methylbutoxy, 1,2-dimethylpropoxy, n-hexyloxy, 1-methylpentyloxy and 2-ethylbutoxy.

Q represents oxygen atom, sulfur atom or —NR— wherein R is hydrogen atom or alkyl such as methyl, ethyl, n-propyl, iso-propyl, n-butyl, iso-butyl, sec-butyl, tert-butyl, n-pentyl, iso-pentyl, sec-pentyl, neopentyl, 1-methylbutyl, 1,2-dimethylpropyl, n-hexyl, 1-methylpentyl and 2-ethylbutyl.

The triphenylphosphine derivative represented by the formula (I) or (II) can be prepared by reacting the compound represented by formula (III):

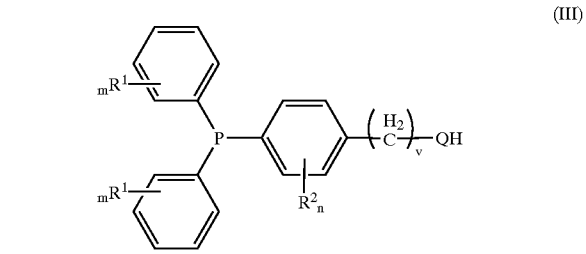

(III)

[in the formula (III), $R^1$ and $R^2$, which may be the same or different, represent hydrogen atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms, fluoroalkyl with 1 to 6 carbon atoms or aminoalkyl with 1 to 3 carbon atoms; m and n independently represent 1 or 2; v represents an integer of 0 to 3; and Q represents oxygen atom, sulfur atom or —NR— where R represents alkyl with 1 to 6 carbon atoms or hydrogen atom], with a hydroxy-containing lactone such as δ-gluconolactone, L-glucono-1,5-lactone, L-gluconic γ-lactone, D-gluconic γ-lactone, α-D-gluconoheptonic γ-lactone and α,β-glucooctanoic γ-lactone. For production in an industrial scale, readily available and inexpensive δ-gluconolactone is preferably used in the light of economic efficiency and stable production. It is preferably used in an amount of 0.5 to 2 moles, more preferably 0.9 to 1.5 moles to 1.0 mole of the compound represented by the formula (III).

The reaction may be conducted using an organic solvent, which may be any solvent without limitations as long as it does not adversely affect the reaction, including amides such as dimethylformamide and dimethylacetamide; pyrrolidones such as N-methyl-2-pyrrolidone; ketones and sulfoxides such as acetone, ethylmethyl ketone and dimethylsulfoxide; aromatic hydrocarbons such as benzene, toluene, xylenes and mesitylene; nitrites such as acetonitrile; ethers such as diisopropyl ether, tetrahydrofuran, 1,4-dioxane, 1,2-dimethoxyethane and anisole; and alcohols such as methanol, ethanol, propanol, ethyleneglycol and propyleneglycol. Its amount to be used is not particularly limited. In an industrial practice, generally, the amount is preferably 5 to 5000 parts by weight, more preferably 50 to 3000 parts by weight to 100 parts by weight of the compound represented by the formula (III) in the light of operability and economic efficiency. The reaction is conducted under an ambient pressure at a temperature preferably in the range of 0° C. to 150° C., more preferably 30° C. to 100° C.

The triphenylphosphine derivative thus obtained may be converted into a phosphine ligand-nickel complex or phosphine ligand-palladium complex by reacting it with a nickel salt or palladium compound, respectively.

Palladium compounds and nickel salts capable of forming a complex with a triphenylphosphine derivative according to this invention as a ligand are described below.

Examples of a palladium salt capable of forming a palladium complex with the triphenylphosphine derivative represented by the formula (I) or (II) include bis(benzylidene) acetone palladium, palladium bisacetylacetonate, dichlorobisacetonitrile palladium, dichlorobisbenzonitrile palladium, dichloro(1,5-cyclooctadiene) palladium, bis(1,5-cyclooctadiene) palladium, tris(dibenzylideneacetone) dipalladium, palladium chloride and palladium acetate, preferably dibromo(1,5-cyclooctadiene) palladium. The amount of the palladium salt is preferably 0.2 to 2.5 moles, more preferably 0.3 to 1.5 moles to 1.0 mole of the triphenylphosphine derivative represented by the formula (I) or (II).

Examples of a nickel salt capable of forming a nickel complex with the triphenylphosphine derivative represented by the formula (I) or (II) include nickel halides such as nickel chloride hexahydrate, anhydrous nickel chloride, nickel bromide trihydrate, anhydrous nickel bromide, nickel iodide hexahydrate and anhydrous nickel iodide; nickel nitrates such as nickel nitrate hexahydrate and anhydrous nickel nitrate; nickel sulfates such as nickel sulfate heptahydrate, anhydrous nickel sulfate and nickel sulfate; nickel organocarboxylates such as nickel acetate tetrahydrate, anhydrous nickel acetate, nickel oxalate dihydrate and anhydrous nickel oxalate; nickel acetylacetonate complex salts such as nickel acetylacetonate dihydrate and anhydrous nickel acetylacetonate; and nickel hydroxide. The amount of the nickel salt is preferably 0.2 to 2.5 moles, more preferably 0.3 to 1.5 moles to 1.0 mole of the triphenylphosphine derivative represented by the formula (I) or (II).

The complex can be prepared in an organic solvent, which may be any solvent without limitations as long as it does not adversely affect the reaction, including amides such as dimethylformamide and dimethylacetamide; pyrrolidones such as N-methyl-2-pyrrolidone; ketones and sulfoxides such as acetone, ethylmethyl ketone and dimethylsulfoxide; aromatic hydrocarbons such as benzene, toluene, xylenes and mesitylene; nitriles such as acetonitrile; ethers such as diisopropyl ether, tetrahydrofuran, 1,4-dioxane, 1,2-dimethoxyethane and anisole; and alcohols such as methanol, ethanol, propanol, ethyleneglycol and propyleneglycol. Its amount to be used is not particularly limited. In an industrial practice, generally, the amount is preferably 5 to 5000 parts by weight, more preferably 50 to 3000 parts by weight to 100 parts by weight of the compound represented by the formula (III) in the light of operability and economic efficiency. The reaction is conducted under an ambient pressure at a temperature preferably in the range of 0° C. to 150° C., more preferably 30° C. to 100° C.

There will be described a process for preparing a biaryl derivative utilizing a complex catalyst prepared from the phosphine ligand as described above and a palladium or nickel compound.

In the presence of a water-soluble palladium or nickel complex catalyst which can be readily prepared from a phosphine ligand to which the water-soluble hydroxy-containing lactone represented by the formula (I) or (II) is added, an aryl halide derivative or aryl sulfonyl derivative represented by formula (IV) is reacted with an arylboronic acid represented by formula (V) or (VI):

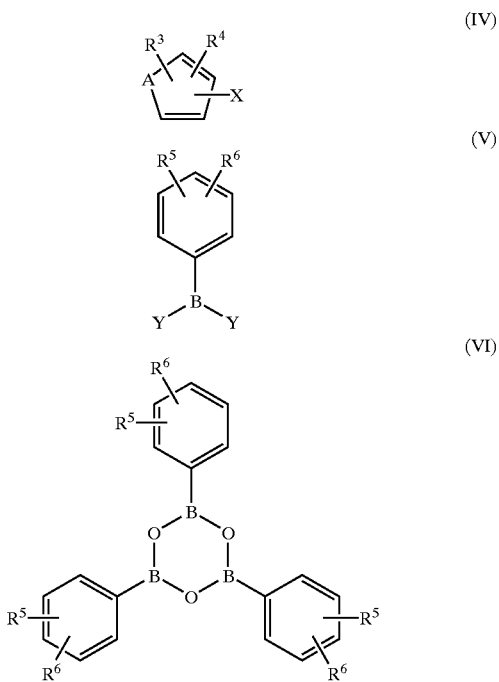

[in the formula (IV), (V) and (VI), A represents S, O, HC=CH or N=CH; $R^3$, $R^4$, $R^5$ and $R^6$ which may the same or different, represent hydrogen atom, chlorine atom, fluorine atom, alkyl with 1 to 6 carbon atoms, phenyl optionally having alkyl with 1 to 6 carbon atoms, alkenyl with 2 to 6 carbon atoms, alkynyl with 2 to 6 carbon atoms, alkoxy with 1 to 6 carbon atoms, alkylthio with 1 to 6 carbon atoms, cyano, formyl, acyl with 2 to 7 carbon atoms, benzoyl optionally having alkyl with 1 to 6 carbon atoms, alkoxycarbonyl with 2 to 7 carbon atoms, phenoxycarbonyl optionally having alkyl with 1 to 6 carbon atoms, amino optionally having alkyl with 1 to 6 carbon atoms, amido optionally having alkyl with 1 to 6 carbon atoms, nitro, sulfonyl having alkyl with 1 to 6 carbon atoms or having phenyl optionally having alkyl with 1 to 6 carbon atoms, sulfonic ester group having alkyl with 1 to 6 carbon atoms or having phenyl optionally having alkyl with 1 to 6 carbon atoms or fluoroalkyl with 1 to 6 carbon atoms; X represents chlorine, bromine, iodine, mesylate or arenesulfonate; Y represents hydroxy, alkoxy with 1 to 6 carbon atoms, phenoxy optionally having alkyl with 1 to 6 carbon atoms or cyclohexyloxy; or two Ys are combined together to form a group represented by formula a, b or c:

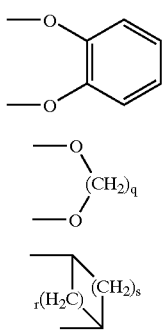

wherein q represents 1, 2, 3 or 4; and r and s independently represent 2, 3, 4 or 5]in water, an organic solvent or a mixture of an organic solvent and water, in the presence of a base, to give a biaryl derivative represented by formula (VII).

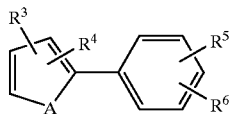

(VII)

The amount of the palladium or nickel complex catalyst used in preparation of the biaryl derivative is preferably 0.00001 to 0.1 moles (converted into the amount of palladium or nickel), more preferably 0.001 to 0.05 moles to 1.0 mole of the aryl halide derivative or aryl sulfonyl derivative.

Examples of the aryl halide derivative or aryl sulfonyl derivative represented by the formula (IV) include chloropyridines such as 2-chloropyridine, 3-chloropyridine and 4-chloropyridine; alkyl substituted chloropyridines such as 2-chloro-3-methylpyridine, 2-chloro-4-methylpyridine, 2-chloro-5-methylpyridine, 2-chloro-3-isopropylpyridine, 3-chloro-2-isopropylpyridine, 3-chloro-4-isopropylpyridine, 3-chloro-5-isopropylpyridine, 4-chloro-2-isopropylpyridine and 4-chloro-3-isopropylpyridine; alkenyl substituted chloropyridines such as 2-chloro-3-isopropenylpyridine, 2-chloro-4-isopropenylpyridine, 2-chloro-5-isopropenylpyridine, 3-chloro-2-isopropenylpyridine, 3-chloro-4-isopropenylpyridine, 3-chloro-5-isopropenylpyridine, 4-chloro-2-isopropenylpyridine and 4-chloro-3-isopropenylpyridine; alkynyl substituted chloropyridines such as 2-chloro-3-ethynylpyridine, 2-chloro-4-ethynylpyridine, 2-chloro-5-ethynylpyridine, 3-chloro-2-ethynylpyridine, 3-chloro-4-ethynylpyridine, 3-chloro-5-ethynylpyridine, 4-chloro-2-ethynylpyridine and 4-chloro-3-ethynylpyridine; aryl substituted chloropyridines such as 2-chloro-3-phenylpyridine, 2-chloro-4-phenylpyridine, 2-chloro-5-phenylpyridine, 3-chloro-2-phenylpyridine, 3-chloro-4-phenylpyridine, 3-chloro-5-phenylpyridine, 4-chloro-2-(p-tolyl)pyridine and 4-chloro-3-phenylpyridine; alkoxy substituted chloropyridines such as 2-chloro-3-methoxypyridine, 2-chloro-4-methoxypyridine, 2-chloro-5-ethoxypyridine, 2-chloro-3-butoxypyridine, 3-chloro-2-isopropoxypyridine, 3-chloro-4-methoxypyridine, 3-chloro-5-ethoxypyridine, 4-chloro-2-methoxypyridine and 4-chloro-3-ethoxypyridine; phenoxy substituted chloropyridines such as 3-chloro-5-phenoxycarbonylpyridine, 4-chloro-2-phenoxycarbonylpyridine and 4-chloro-3-phenoxycarbonylpyridine; benzoyl substituted chloropyridines such as 4-chloro-3-benzoylpyridine and 4-chloro-2-benzoylpyridine; alkylthio substituted chloropyridines such as 2-chloro-3-methylthiopyridine, 2-chloro-4-methylthiopyridine, 2-chloro-5-methylthiopyridine, 2-chloro-3-isopropylthiopyridine, 3-chloro-2-isopropylthiopyridine, 3-chloro-4-isopropylthiopyridine, 3-chloro-5-isopropylthiopyridine, 4-chloro-2-isopropylthiopyridine and 4-chloro-3-isopropylthiopyridine; acyl substituted chloropyridines such as 3-chloro-5-acetylpyridine, 4-chloro-2-acetylpyridine and 4-chloro-3-acetylpyridine; cyano substituted chloropyridines such as 3-chloro-2-cyanopyridine, 3-chloro-4-cyanopyridine, 3-chloro-5-cyanopyridine, 4-chloro-2-cyanopyridine and 4-chloro-3-cyanopyridine; formyl substituted chloropyridines such as 3-chloro-2-formylpyridine, 3-chloro-4-formylpyridine, 3-chloro-5-formylpyridine, 4-chloro-2-formylpyridine and 4-chloro-3-formylpyridine; nitro substituted chloropyridines such as 3-chloro-2-nitropyridine, 3-chloro-4-nitropyridine, 3-chloro-5-nitropyridine, 4-chloro-2-nitropyridine and 4-chloro-3-nitropyridine; alkoxycarbonyl substituted chloropyridines such as 3-chloro-2-methoxycarbonylpyridine, 3-chloro-4-methoxycarbonylpyridine, 3-chloro-5-methoxycarbonylpyridine, 4-chloro-2-butoxycarbonylpyridine and 4-chloro-3-methoxycarbonylpyridine; amino substituted chloropyridines such as 3-chloro-4-aminopyridine, 3-chloro-5-dimethylaminopyridine, 4-chloro-2-dimethylaminopyridine and 4-chloro-3-dimethylaminopyridine; amide substituted chloropyridines such as 3-chloro-4-carbamoylpyridine, 3-chloro-5-dimethylcarbamoylpyridine, 4-chloro-2-dimethylcarbamoylpyridine and 4-chloro-3-dimethylcarbamoylpyridine; sulfonyl substituted chloropyridines such as 4-chloro-2- (p-tolyl) sulfonylpyridine and 4-chloro-3-methylsulfonylpyridine; and fluoroalkyl substituted chloropyridines such as 3-chloro-4-trifluoromethylpyridine, 3-chloro-5-trifluoromethylpyridine, 4-chloro-2-trifluoromethylpyridine and 4-chloro-3-trifluoromethylpyridine. Also can be used bromopyridines such as 2-bromo-pyridine, 3-bromo-pyridine and 4-bromo-pyridine; alkyl substituted bromopyridines such as 2-bromo-3-methylpyridine, 2-bromo-4-methylpyridine, 2-bromo-5-methylpyridine, 2-bromo-3-isopropylpyridine, 3-bromo-2-isopropylpyridine, 3-bromo-4-isopropylpyridine, 3-bromo-5-isopropylpyridine, 4-bromo-2-isopropylpyridine and 4-bromo-3-isopropylpyridine; alkenyl substituted bromopyridines such as 2-bromo-3-isopropenylpyridine, 2-bromo-4-isopropenylpyridine, 2-bromo-5-isopropenylpyridine, 3-bromo-2-isopropenylpyridine, 3-bromo-4-isopropenylpyridine, 3-bromo-5-isopropenylpyridine, 4-bromo-2-isopropenylpyridine and 4-bromo-3-isopropenylpyridine; alkynyl substituted bromopyridines such as 2-bromo-3-ethynylpyridine, 2-bromo-4-ethynylpyridine, 2-bromo-5-ethynylpyridine, 3-bromo-2-ethynylpyridine, 3-bromo-4-ethynylpyridine, 3-bromo-5-ethynylpyridine, 4-bromo-2-ethynylpyridine and 4-bromo-3-ethynylpyridine; aryl substituted bromo-pyridines such as 2-bromo-3-phenylpyridine, 2-bromo-4-phenylpyridine, 2-bromo-5-phenylpyridine, 3-bromo-2-phenylpyridine, 3-bromo-4-phenylpyridine, 3-bromo-5-phenylpyridine, 4-bromo-2-(p-tolyl)pyridine and 4-bromo-3-phenylpyridine; alkoxy substituted bromopyridines such as 2-bromo-3-methoxypyridine, 2-bromo-4-methoxypyridine, 2-bromo-5-ethoxypyridine, 2-bromo-3-butoxypyridine, 3-bromo-2-isopropoxypyridine, 3-bromo-4-methoxypyridine, 3-bromo-5-ethoxypyridine, 4-bromo-2-methoxypyridine and 4-bromo-3-ethoxypyridine; phenoxy substituted bromopyridines such as 3-bromo-5-phenoxycarbonylpyridine, 4-bromo-2-phenoxycarbonylpyridine and 4-bromo-3-phenoxycarbonylpyridine; benzoyl substituted bromopyridines such as 4-bromo-3-benzoylpyridine and 4-bromo-2-benzoylpyridine; alkylthio substituted bromopyridines such as 2-bromo-3-methylthiopyridine, 2-bromo-4-methylthiopyridine, 2-bromo-5-methylthiopyridine, 2-bromo-3-isopropylthiopyridine, 3-bromo-2-isopropylthiopyridine, 3-bromo-4-isopropylthiopyridine, 3-bromo-5-isopropylthiopyridine, 4-bromo-2-isopropylthiopyridine and 4-bromo-3-isopropylthiopyridine; acyl substituted bromopyridines such as 3-bromo-5-acetylpyridine, 4-bromo-2-acetylpyridine and 4-bromo-3-acetylpyridine; cyano substituted bromopyridines such as 3-bromo-2-cyanopyridine, 3-bromo-4-cyanopyridine, 3-bromo-5-cyanopyridine, 4-bromo-2-cyanopyridine and 4-bromo-3-cyanopyridine; formyl substituted bromopyridines such as 3-bromo-2-formylpyridine, 3-bromo-4-formylpyridine, 3-bromo-5-formylpyridine, 4-bromo-2-formylpyridine and 4-bromo-3-formylpyridine; nitro substituted bromopyridines such as 3-bromo-2-nitropyridine, 3-bromo-4-nitropyridine, 3-bromo-5-nitropyridine, 4-bromo-2-nitropyridine and 4-bromo-3-nitropyridine; alkoxycarbonyl substituted bromopyridines such as 3-bromo-2-methoxycarbonylpyridine, 3-bromo-4-methoxycarbonylpyridine, 3-bromo-5-methoxycarbonylpyridine, 4-bromo-2-butoxycarbonylpyridine and 4-bromo-3-methoxycarbonylpyridine; amino substituted bromopyridines such as 3-bromo-4-aminopyridine, 3-bromo-5-dimethylaminopyridine, 4-bromo-2-dimethylaminopyridine and 4-bromo-3-dimethylaminopyridine; amide substituted bromopyridines such as 3-bromo-4-carbamoylpyridine, 3-bromo-5-dimethylcarbamoylpyridine, 4-bromo-2-dimethylcarbamoylpyridine and 4-bromo-3-dimethylcarbamoylpyridine; sulfonyl substituted bromopyridines such as 4-bromo-2-(p-tolyl)sulfonylpyridine and 4-bromo-3-methylsulfonylpyridine; fluoroalkyl substituted bromopyridines such as 3-bromo-4-trifluoromethylpyridine, 3-bromo-5-trifluoromethylpyridine, 4-bromo-2-trifluoromethylpyridine and 4-bromo-3-trifluoromethylpyridine; iodopyridines such as 2-iodopyridine, 3-iodopyridine and 4-iodopyridine; alkyl substituted iodopyridines such as 2-iodo-3-methylpyridine, 2-iodo-4-methylpyridine, 2-iodo-5-methylpyridine, 2-iodo-3-isopropylpyridine, 3-iodo-2-isopropylpyridine, 3-iodo-4-isopropylpyridine, 3-iodo-5-isopropylpyridine, 4-iodo-2-isopropylpyridine and 4-iodo-3-isopropylpyridine; alkenyl substituted iodopyridines such as 2-iodo-3-isopropenylpyridine, 2-iodo-4-isopropenylpyridine, 2-iodo-5-isopropenylpyridine, 3-iodo-2-isopropenylpyridine, 3-iodo-4-isopropenylpyridine, 3-iodo-5-isopropenylpyridine, 4-iodo-2-isopropenylpyridine and 4-iodo-3-isopropenylpyridine; alkynyl substituted iodopyridines such as 2-iodo-3-ethynylpyridine, 2-iodo-4-ethynylpyridine, 2-iodo-5-ethynylpyridine, 3-iodo-2-ethynylpyridine, 3-iodo-4-ethynylpyridine, 3-iodo-5-ethynylpyridine, 4-iodo-2-ethynylpyridine and 4-iodo-3-ethynylpyridine; aryl substituted iodo-pyridines such as 2-iodo-3-phenylpyridine, 2-iodo-4-phenylpyridine, 2-iodo-5-phenylpyridine, 3-iodo-2-phenylpyridine, 3-iodo-4-phenylpyridine, 3-iodo-5-phenylpyridine, 4-iodo-2-(p-tolyl)pyridine and 4-iodo-3-phenylpyridine; alkoxy substituted iodopyridines such as 2-iodo-3-methoxypyridine, 2-iodo-4-methoxypyridine, 2-iodo-5-ethoxypyridine, 2-iodo-3-butoxypyridine, 3-iodo-2-isopropoxypyridine, 3-iodo-4-methoxypyridine, 3-iodo-5-ethoxypyridine, 4-iodo-2-methoxypyridine and 4-iodo-3-ethoxypyridine; phenoxy substituted iodopyridines such as 3-iodo-5-phenoxycarbonylpyridine, 4-iodo-2-phenoxycarbonylpyridine and 4-iodo-3-phenoxycarbonylpyridine; benzoyl substituted iodopyridines such as 4-iodo-3-benzoylpyridine and 4-iodo-2-benzoylpyridine; alkylthio substituted iodopyridines such as 2-iodo-3-methylthiopyridine, 2-iodo-4-methylthiopyridine, 2-iodo-5-methylthiopyridine, 2-iodo-3-isopropylthiopyridine, 3-iodo-2-isopropylthiopyridine, 3-iodo-4-isopropylthiopyridine, 3-iodo-5-isopropylthiopyridine, 4-iodo-2-isopropylthiopyridine and 4-iodo-3-isopropylthiopyridine; acyl substituted iodopyridines such as 3-iodo-5-acetylpyridine, 4-iodo-2-acetylpyridine and 4-iodo-3-acetylpyridine; cyano substituted iodo-pyridines such as 3-iodo-2-cyanopyridine, 3-iodo-4-cyanopyridine, 3-iodo-5-cyanopyridine, 4-iodo-2-cyanopyridine and 4-iodo-3-cyanopyridine; formyl substituted iodopyridines such as 3-iodo-2-formylpyridine, 3-iodo-4-formylpyridine, 3-iodo-5-formylpyridine, 4-iodo-2-formylpyridine and 4-iodo-3-formylpyridine; nitro substituted iodopyridines such as 3-iodo-2-nitropyridine, 3-iodo-4-nitropyridine, 3-iodo-5-nitropyridine, 4-iodo-2-nitropyridine and 4-iodo-3-nitropyridine; alkoxycarbonyl substituted iodo-pyridines such as 3-iodo-2-methoxycarbonylpyridine, 3-iodo-4-methoxycarbonylpyridine, 3-iodo-5-methoxycarbonylpyridine, 4-iodo-2-butoxycarbonylpyridine and 4-iodo-3-methoxycarbonylpyridine; amino substituted iodopyridines such as 3-iodo-4-aminopyridine, 3-iodo-5-dimethylaminopyridine, 4-iodo-2-dimethylaminopyridine and 4-iodo-3-dimethylaminopyridine; amide substituted iodo-pyridines such as 3-iodo-4-carbamoylpyridine, 3-iodo-5-dimethylcarbamoylpyridine, 4-iodo-2-dimethylcarbamoylpyridine and 4-iodo-3-dimethylcarbamoylpyridine; sulfonyl substituted iodopyridines such as 4-iodo-2-(p-tolyl)sulfonylpyridine and 4-iodo-3-methylsulfonylpyridine; fluoroalkyl substituted iodopyridines such as 3-iodo-4-trifluoromethylpyridine, 3-iodo-5-trifluoromethylpyridine, 4-iodo-2-trifluoromethylpyridine and 4-iodo-3-trifluoromethylpyridine; mesylpyridines such as 2-mesylpyridine, 3-mesylpyridine and 4-mesylpyridine; alkyl substituted mesylpyridines such as 2-mesyl-3-methylpyridine, 2-mesyl-4-methylpyridine, 2-mesyl-5-methylpyridine, 2-mesyl-3-isopropylpyridine, 3-mesyl-2-isopropylpyridine, 3-mesyl-4-isopropylpyridine, 3-mesyl-5-isopropylpyridine, 4-mesyl-2-isopropylpyridine and 4-mesyl-3-isopropylpyridine; alkenyl substituted mesylpyridines such as 2-mesyl-3-isopropenylpyridine, 2-mesyl-4-isopropenylpyridine, 2-mesyl-5-isopropenylpyridine, 3-mesyl-2-isopropenylpyridine, 3-mesyl-4-isopropenylpyridine, 3-mesyl-5-isopropenylpyridine, 4-mesyl-2-isopropenylpyridine and 4-mesyl-3-isopropenylpyridine; alkynyl substituted mesylpyridines such as 2-mesyl-3-ethynylpyridine, 2-mesyl-4-ethynylpyridine, 2-mesyl-5-ethynylpyridine, 3-mesyl-2-ethynylpyridine, 3-mesyl-4-ethynylpyridine, 3-mesyl-5-ethynylpyridine, 4-mesyl-2-ethynylpyridine and 4-mesyl-3-ethynylpyridine; aryl substituted mesylpyridines such as 2-mesyl-3-phenylpyridine, 2-mesyl-4-phenylpyridine, 2-mesyl-5-phenylpyridine, 3-mesyl-2-phenylpyridine, 3-mesyl-4-phenylpyridine, 3-mesyl-5-phenylpyridine, 4-mesyl-2-(p-tolyl)pyridine and 4-mesyl-3-phenylpyridine; alkoxy substituted mesylpyridines such as 2-mesyl-3-methoxypyridine, 2-mesyl-4-methoxypyridine, 2-mesyl-5-ethoxypyridine, 2-mesyl-3-butoxypyridine, 3-mesyl-2-isopropoxypyridine, 3-mesyl-4-methoxypyridine, 3-mesyl-5-ethoxypyridine, 4-mesyl-2-methoxypyridine and 4-mesyl-3-ethoxypyridine; phenoxy substituted mesylpyridines such as 3-mesyl-5-phenoxycarbonylpyridine, 4-mesyl-2-phenoxycarbonylpyridine and 4-mesyl-3-phenoxycarbonylpyridine; benzoyl substituted mesylpyridines such as 4-mesyl-3-benzoylpyridine and 4-mesyl-2-benzoylpyridine; alkylthio substituted mesylpyridines such as 2-mesyl-3-methylthiopyridine, 2-mesyl-4-methylthiopyridine, 2-mesyl-5-methylthiopyridine, 2-mesyl-3-isopropylthiopyridine, 3-mesyl-2-isopropylthiopyridine, 3-mesyl-4-isopropylthiopyridine, 3-mesyl-5-isopropylthiopyridine, 4-mesyl-2-isopropylthiopyridine and 4-mesyl-3-isopropylthiopyridine; acyl substituted mesylpyridines such as 3-mesyl-5-acetylpyridine, 4-mesyl-2-acetylpyridine and 4-mesyl-3-acetylpyridine; cyano substituted mesylpyridines such as 3-mesyl-2-cyanopyridine, 3-mesyl-4-cyanopyridine, 3-mesyl-5-cyanopyridine, 4-mesyl-2-cyanopyridine and 4-mesyl-3-cyanopyridine; formyl substituted mesylpyridines such as 3-mesyl-2-formylpyridine, 3-mesyl-4-formylpyridine, 3-mesyl-5-formylpyridine, 4-mesyl-2-formylpyridine and 4-mesyl-3-formylpyridine; nitro substituted mesylpyridines such as 3-mesyl-2-nitropyridine, 3-mesyl-4-nitropyridine, 3-mesyl-5-nitropyridine, 4-mesyl-2-nitropyridine and 4-mesyl-3-nitropyridine; alkoxycarbonyl substituted mesylpyridines such as 3-mesyl-2-methoxycarbonylpyridine, 3-mesyl-4-methoxycarbonylpyridine, 3-mesyl-5-methoxycarbonylpyridine, 4-mesyl-2-butoxycarbonylpyridine and 4-mesyl-3-methoxycarbonylpyridine; amino substituted mesylpyridines such as 3-mesyl-4-aminopyridine, 3-mesyl-5-dimethylaminopyridine, 4-mesyl-2-dimethylaminopyridine and 4-mesyl-3-dimethylaminopyridine; amide substituted mesylpyridines such as 3-mesyl-4-carbamoylpyridine, 3-mesyl-5-dimethylcarbamoylpyridine, 4-mesyl-2-dimethylcarbamoylpyridine and 4-mesyl-3-dimethylcarbamoylpyridine; and fluoroalkyl substituted mesylpyridines such as 3-mesyl-4-trifluoromethylpyridine, 3-mesyl-5-trifluoromethylpyridine, 4-mesyl-2-trifluoromethylpyridine and 4-mesyl-3-trifluoromethylpyridine.

Examples of the arylboronic acid represented by the formula (V) or (VI) include esters of the above boronic acids such as alkyl esters and phenyl esters; for example, alkyl substituted phenylboronic acids such as phenylboronic acid, p-methylphenylboronic acid and m-isopropylphenylboronic acid; alkenyl substituted phenylboronic acids such as p-isopropenylphenylboronic acid; alkynyl substituted phenylboronic acids such as p-ethynylphenylboronic acid; aryl substituted phenylboronic acids such as p-biphenylboronic acid; alkoxy substituted phenylboronic acids such as m-methoxyphenylboronic acid and p-butoxyphenylboronic acid; alkylthio substituted phenylboronic acids such as p-methylthiophenylboronic acid; cyano substituted phenylboronic acids; formyl substituted phenylboronic acids; nitro substituted phenylboronic acids; acyl substituted phenylboronic acids such as p-acetylphenylboronic acids; aroyl substituted phenylboronic acids such as p-benzoylphenylboronic acid; alkoxycarbonyl substituted phenylboronic acids such as p-methoxycarbonylphenylboronic acid; phenoxycarbonyl substituted phenylboronic acids such as p-methylphenoxycarbonylphenylboronic acid; amino substituted phenylboronic acids such as p-aminophenylboronic acid and p-dimethylaminophenylboronic acid; amide substituted phenylboronic acids such as p-carbamoylphenylboronic acid and p-monomethylcarbamoylphenylboronic acid; sulfonyl substituted phenylboronic acids such as p-methylsulfonylphenylboronic acid and p-tolylsulfonylphenylboronic acid; fluorophenylboronic acids; and fluoroalkyl substituted phenylboronic acids such as trifluoromethylphenylboronic acid. The anhydride of the boronic acid represented by the formula (VI) is an anhydride of one of the above boronic acids. These aryboronic acids and boronic acid andyrides may be without limitations used in combination of two or more.

As for the proportion of the aryl halide derivative or aryl sulfonyl derivative represented by the formula (IV) and the arylboronic acid represented by the formula (V) to be reacted, generally, the arylboronic acid or its derivative is used in an amount of preferably 0.8 to 1.5 moles, more preferably 1 to 1.3 moles to 1 mole of the aryl halide derivative or aryl sulfonyl derivative in the light of economic efficiency and reactivity. As for the proportion of the aryl halide derivative or aryl sulfonyl derivative and arylboronic acid anhydride represented by the formula (VI), similarly, the aryl boronic acid anhydride is used in an amount of preferably 0.3 to 0.5 moles, more preferably 0.33 to 0.43 moles to 1 mole of the aryl halide derivative or aryl sulfonyl derivative.

A solvent used in preparation of the biaryl derivative may be any of those which do not adversely affect the reaction; for example, amides such as dimethylformamide and dimethylacetamide; pyrrolidones such as N-methyl-2-pyrrolidone; ketones and sulfoxides such as acetone, ethylmethyl ketone and dimethylsulfoxide; aromatic hydrocarbons such as benzene, toluene, xylenes and mesitylene; nitriles such as acetonitrile; ethers such as diisopropyl ether, tetrahydrofuran, 1,4-dioxane, 1,2-dimethoxyethaneandanisole; alcohols such as methanol, ethanol, propanol, ethyleneglycol and propyleneglycol; and water. In industrial practice, its amount is preferably 5 to 5000 parts by weight, more preferably about 50 to 3000 parts by weight to 100 parts by weight of the aryl halide derivative or aryl sulfonyl derivative in the light of operability and economic efficiency. These solvents may be used alone or in combination, as appropriate.

The amount of water is preferably 5 to 5000 parts by weight, more preferably about 50 to 3000 parts by weight to 100 parts by weight of the chloropyridine derivative.

Examples of a base used include alkali metal hydroxides and their salts with a weak acid; alkaline earth metal hydroxides and their salts with a weak acid; and quaternary ammonium hydroxides and their salts with a weak acid. Preferable examples include sodiumhydroxide, potassiumhydroxide, sodium carbonate, sodiumbicarbonate, potassiumcarbonate, potassiumbicarbonate, cesium carbonate, tripotassium phosphate and tripotassium phosphate dihydrate. The amount of the base is preferably 0.2 to 5 moles, more preferably 1 to 3 moles to 1 mole of the aryl halide derivative or aryl sulfonyl derivative.

The reaction is conducted at a temperature in the range of preferably −20 to 180° C. in general, more preferably 60 to 140° C. A reaction period generally depends on some factors such as a reaction temperature and the amount of the catalyst, but is preferably 0.2 to 120 hours in general, more preferably 2 to 24 hours. For preventing the catalyst from being inactivated by oxygen during the reaction, the reaction is preferably conducted under an atmosphere of an inert gas such as nitrogen gas and argon gas. A reaction pressure is generally, but not limited to, an atmospheric pressure.

According to a process of this invention, by using a water-soluble complex catalyst which can be readily prepared from the triphenylphosphine derivative represented by the formula (I) or (II) for the reaction, and successively washing with water, the catalyst and a phosphorous compound can be easily separated without contamination with palladium or phosphorous compounds to give a biaryl derivative with a higher purity. This feature is industrially extremely useful.

The biaryl derivative represented by formula (VII) which is the desired compound of this invention can be prepared as described above. Preferably, known processes such as washing using, e. g., an aqueous alkali solution or a saturated brine, acid precipitation, concentration, recrystallization and crystallization may be conducted for improving a purity of the biaryl derivative. A reaction product may be treated with silica gel or alumina.

N-(4-diphenylphosphinophenyl)methyl gluconamide (GLCAphos) which is a triphenylphosphine derivative of this invention can be applied not only to preparation of a biaryl derivative but also to other reactions such as Heck reaction (equation (VIII)), carbonylation (equation (IX)), hydroformylation (equation (X)), hydrogenation (equation (XI)) and asymmetric hydrogenation (equation (XII)). A technique that a hydroxy-containing lactone is added to a lipophilic triphenylphosphine derivative ligand of this invention to form a water-soluble ligand may be applied not only to preparation of a triphenylphosphine derivative but also to converting an asymmetric ligand such as BINAP (formula (XIII)) and MOP (MAP) (formula (XIV)) into a water-soluble ligand. A complex of the ligand with a metal may be used, for example, for asymmetric hydrogenation.

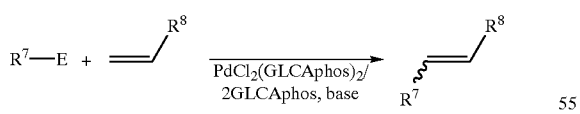
(VIII)

($R^7$ represents alkyl, alkenyl or aryl; E represents Cl, Br or I; $R^8$ represents H, alkyl, aryl, CN, CHO, C(O)$R^9$, C(O)NR$^9_2$, CO$_2R^9$, CO$_2$H, NO$_2$, NH$_2$, NR$_2$, OR$^9$ or F; and $R^9$ represents alkyl, alkenyl or aryl.)

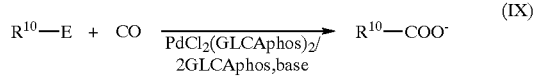
(IX)

($R^{10}$ represents alkyl, alkenyl or aryl; and E represents Cl, Br or I.)

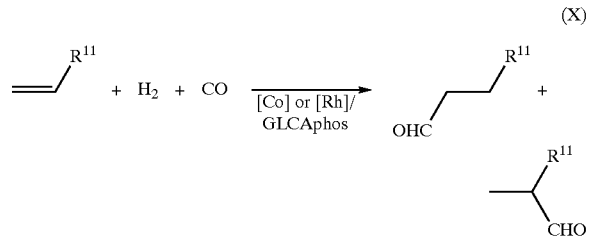
(X)

($R^{11}$ represents H, alkyl, alkenyl or aryl.)

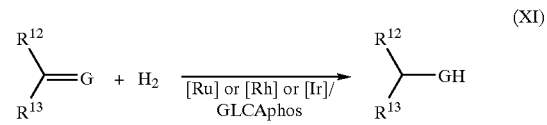
(XI)

($R^{12}$ and $R^{13}$, which are the same or different, represent H, alkyl, alkenyl or aryl; and G represents CH$_2$, NH or O.)

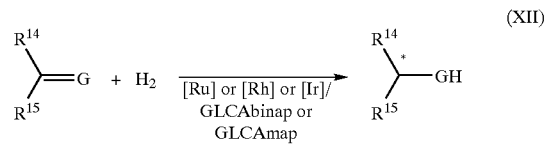
(XII)

($R^{12}$ and $R^{13}$, which are different from each other, represent H, alkyl, alkenyl or aryl; and G represents CH$_2$, NH or O.)

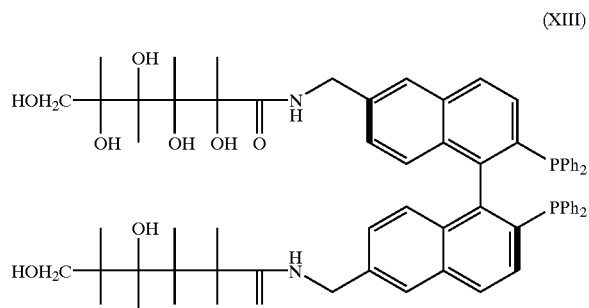
(XIII)

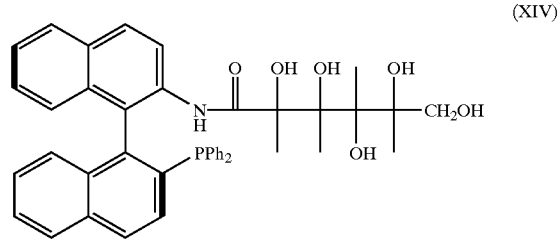
(XIV)

This invention will be described with reference to, but not limited to, Examples.

EXAMPLE 1

Synthesis of N-(4-diphenylphosphinophenyl)methyl gluconamide: GLCAphos

In a flask were placed (4-aminomethylphenyl)diphenylphosphine (2.89 g, 9.9 mmol), D-glucono-1,5-lactone (1.78 g, 10 mmol) and drybenzene (60 ml), and the mixture was heated at 80° C. for two hours with stirring, during which precipitate was formed. After cooling to room temperature, the precipitate was collected by vacuum filtration. The collected solid was washed with 10 mL of benzene five times. The product was dried at room temperature in vacuo. Yield: 4.46 g (96%).

The compound thus prepared is abbreviated to GLCAphos.

$^1$H NMR (400 MHz, CD$_3$OD) 3.62 (dd, J=5.8, 11.0 Hz, 1H), 3.68–3.76 (m, 2H), 3.78 (dd, J=3.4, 11.2 Hz, 1H), 4.15 (dd, J=2.9, 5.8 Hz, 1H), 4.28 (d, J=3.4 Hz, 1H), 4.42 (d, J=15.4 Hz, 1H), 4.49 (d, J=15.4 Hz, 1H), 7.19–7.26 (m, 6H), 7.31–7.35 (m, 8H); $^{13}$C NMR (100 MHz, CD$_3$OD) d 43.36, 64.65, 71.83, 72.93, 74.31, 75.49, 128.54, 128.62, 129.57, 129.64, 129.94, 134.52, 134.72, 134.82, 135.02, 136.94, 138.52, 140.79, 175.33.

Example 2
Preparation of (GLCAphos)$_2$PdCl$_2$

In a flask were placed PdCl$_2$(cod) (cod represents 1,5-cyclooctadiene) (0.172 g, 0.6 mmol), GLCAphos (0.62 g, 1.3 mmol) and dry acetonitrile (25 ml) and the mixture was heated at 100° C. for 1 hour with stirring. During the initial period of heating all the solids were dissolved and then a pale brown solid was gradually precipitated. After cooling to room temperature, the solid was collected by filtration, sequentially washed with acetonitrile and ether, and finally dried in vacuo to give (GLCAphos)$_2$PdCl$_2$ in a quantitative yield.

Example 3
Preparation of 4-methoxy-4'-methylbiphenyl

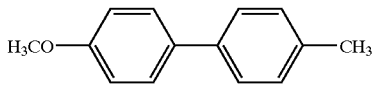

In a reaction vessel were placed p-tolylboronic acid (0.177 g, 1.3 mmol) and (GLCAphos)$_2$PdCl$_2$ (11 mg, 0.01 mmol), and the atmosphere was replaced with argon. To the mixture were added water (2 ml), an aqueous solution of sodium carbonate (2M solution, 1 ml, 2 mmol) and 4-methoxybromobenzene (0.125 ml, 1.0 mmol) as an aryl halide derivative at room temperature and the mixture was heated at 80° C. with stirring for 16 hours. During the reaction, a white solid was gradually precipitated. After cooling to room temperature, toluene (10 ml) was added to extract the product. The organic layer was washed with water five times and dried under a reduced pressure to give a substantially pure 4-methoxy-4'-methylbiphenyl in an yield of 95%.

Example 4
Preparation of 2-(p-tolyl)pyridine

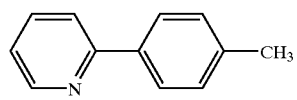

The process described in Example 3 was conducted except using 2-bromopyridine as an aryl halide derivative. The amount of the aryl halide derivative was the same molar amount as that in Example 3. An yield of 2-(p-tolyl)pyridine was 85%.

Example 5
Preparation of 4-hydroxycarbonyl-4'-methylbiphenyl

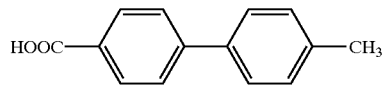

The process described in Example 3 was conducted except using 4-bromobenzoic acid as an aryl halide derivative. The amount of the aryl halide derivative was the same molar amount as that in Example 3. An yield of 4-hydroxycarbonyl-4'-methylbiphenyl was 71%.

Example 6
Preparation of 4-dimethylamino-4'-methylbiphenyl

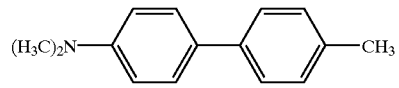

The process described in Example 3 was conducted except using 4-bromodimethylaniline as an aryl halide derivative. The amount of the aryl halide derivative was the same molar amount as that in Example 3. An yield of 4-dimethylamino-4'-methylbiphenyl was 74%.

Example 7
Preparation of 4-fluoro-4'-methylbiphenyl

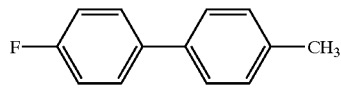

The process described in Example 3 was conducted except using 4-bromofuluorobenzene as an aryl halide derivative. The amount of the aryl halide derivative was the same molar amount as that in Example 3. An yield of 4-fluoro-4'-methylbiphenyl was 95%.

Example 8
Preparation of 4-nitro-4'-methylbiphenyl

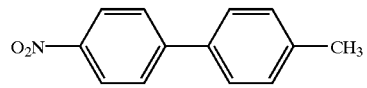

The process described in Example 3 was conducted except using 4-bromonitrobenzene as an aryl halide derivative. The amount of the aryl halide derivative was the same molar amount as that in Example 3. An yield of 4-nitro-4'-methylbiphenyl was 96%.

Example 9
Preparation of 4-hydroxy-4'-methylbiphenyl

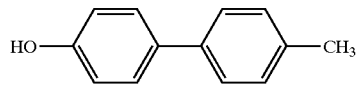

The process described in Example 3 was conducted except using 4-bromohydroxybenzene as an aryl halide derivative. The amount of the aryl halide derivative was the same molar amount as that in Example 3. An yield of 4-hydroxy-4'-methylbiphenyl was 99%.

Example 10
Preparation of 4-acetyl-4'-methylbiphenyl

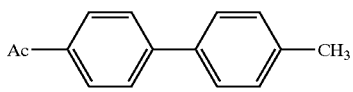

The process described in Example 3 was conducted except using 4-chloroacetophenone as an aryl halide derivative. The amount of the aryl halide derivative was the same molar amount as that in Example 3. An yield of 4-acetyl-4'-methylbiphenyl was 51%.

Example 11

Preparation of 4-formyl-4'-methylbiphenyl

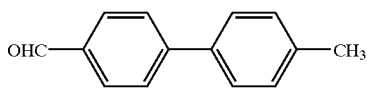

The process described in Example 3 was conducted except using 4-chlorobenzaldehyde as an aryl halide derivative. The amount of the aryl halide derivative was the same molar amount as that in Example 3. An yield of 4-formyl-4'-methylbiphenyl was 93%.

Example 12
Preparation of 4-methanesulfonyloxy-4'-methylbiphenyl

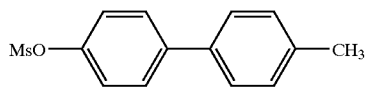

The process described in Example 3 was conducted except using 4-iodomethanesulfonyloxybenzene as an aryl halide derivative. The amount of the aryl halide derivative was the same molar amount as that in Example 3. An yield of 4-methanesulfonyloxy-4'-methylbiphenyl was 99%

Example 13
Preparation of 3-(p-tolyl)pyridine

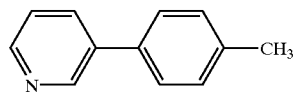

The process described in Example 3 was conducted except using 3-bromopyridine as an aryl halide derivative. The amount of the aryl halide derivative was the same molar amount as that in Example 3. An yield of 3-(p-tolyl)pyridine was 89%.

INDUSTRIAL APPLICABILITY

According to a preparation process of this invention, a triphenylphosphine derivative ligand to which a water-soluble hydroxy-containing lactone is added and a water-soluble complex catalyst derived therefrom can be readily prepared. This invention provides an economically efficient, convenient and industrially superb process having the features that a biaryl derivative represented by the formula (VII) can be obtained using one of various aryl halides derivative or aryl sulfonyl derivative in a higher yield; that a product can be easily separated from a catalyst by a simple procedure such as washing with water; and that the amount of the catalyst is vary small.

What is claimed is:

1. A triphenyl phosphine derivative represented by formula (I):

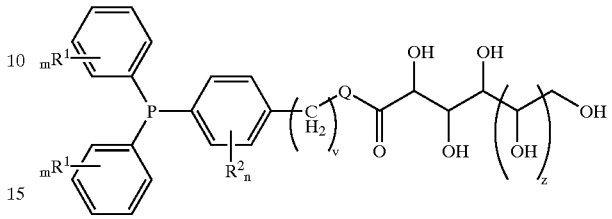

wherein $R^1$ and $R^2$, which may be the same or different, each independently represent a hydrogen atom, a fluorine atom, a $C_1$–$C_6$ alkyl group, a phenyl group optionally substituted with $C_1$–$C_6$ alkyl, a $C_2$–$C_6$ alkenyl group, a $C_2$–$C_6$ alkynyl group, a $C_1$–$C_6$ alkoxy group, a $C_1$–$C_6$ alkylthio group, a cyano group, a formyl group a $C_2$–$C_7$ acyl group, a benzoyl group optionally substituted with $C_1$–$C_6$ alkyl, a $C_2$–$C_7$ alkoxycarbonyl group, a phenoxycarbonyl group optionally substituted by $C_1$–$C_6$ alkyl, an amino group optionally substituted by $C_1$–$C_6$ alkyl, an amido group optionally substituted by $C_1$–$C_6$ alkyl, a nitro group, a sulfonyl group substituted by $C_1$–$C_6$ alkyl or substituted by a phenyl group optionally substituted by $C_1$–$C_6$ alkyl, a sulfonic ester group substituted by $C_1$–$C_6$ alkyl or substituted by a phenyl group optionally substituted by $C_1$–$C_6$ alkyl, a $C_1$–$C_6$ fluoroalkyl group or a $C_1$–$C_3$ aminoalkyl group;

m and n independently represent 1 or 2;

v represents an integer of 0 to 3;

z represents 1 or 2; and

Q represents an oxygen atom, sulfur atom or —NR— where R represents $C_1$–$C_6$ alkyl.

2. The triphenyl phosphine derivative of claim 1 represented by formula (II):

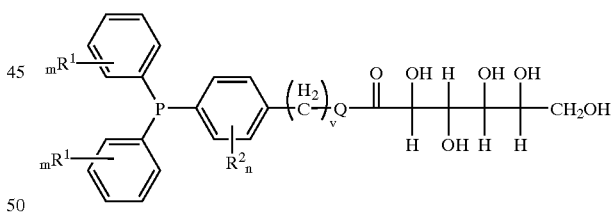

wherein $R^1$ and $R^2$, which may be the same or different, each independently represent a hydrogen atom, a fluorine atom, $C_1$–$C_6$ alkyl group, a phenyl group optionally substituted with $C_1$–$C_6$ alkyl, a $C_2$–$C_6$ alkenyl group, a $C_2$–$C_6$ alkynyl group, a $C_1$–$C_6$ alkoxy group, a $C_1$–$C_6$ alkylthio group, a cyano group, a formyl group, a $C_2$–$C_7$ acyl group, a benzoyl group optionally substituted with $C_1$–$C_6$ alkyl, a $C_2$–$C_7$ alkoxycarbonyl group, a phenoxycarbonyl group optionally substituted with $C_1$–$C_6$ alkyl, an amino group optionally substituted with $C_1$–$C_6$ alkyl, an amido group optionally substituted with $C_1$–$C_6$ a nitro group, a sulfonyl group substituted with $C_1$–$C_6$ alkyl or substituted with a phenyl group optionally substituted with $C_1$–$C_6$ alkyl, a sulfonic ester group substituted with $C_1$–$C_6$ alkyl or a phenyl group optionally substituted with $C_1$–$C_6$ alkyl, a $C_1$–$C_6$ fluoroalkyl group or a $C_1$–$C_3$ aminoalkyl group;

m and n independently represent 1 or 2;

v represents an integer of 0 to 3; and

Q represents oxygen atom, sulfur atom or —NR— where R represents $C_1$–$C_6$ alkyl.

3. The triphenyl phosphine derivative of claim 2, wherein in formula (II), $R^1$ and $R^2$ represent hydrogen;

m, n and v represent 1; and

Q represents —NR—$_4$ where R represents $C_1$–$C_6$ alkyl.

4. A process for preparing the triphenyl phosphine derivative of claim 1 by:

reacting a hydroxy-containing lactone with a compound represented by formula (III):

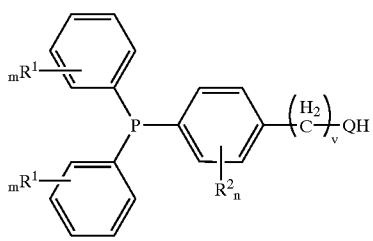

wherein $R^1$ and $R^2$, which may be the same or different, independently represent a hydrogen atom, a fluorine atom, a $C_1$–$C_6$ alkyl group, a phenyl group optionally substituted by $C_1$–$C_6$ alkyl, a $C_2$–$C_6$ alkenyl group, a $C_2$–$C_6$ alkynyl group, a $C_1$–$C_6$ alkoxy group, a $C_1$–$C_6$ alkylthio, a cyano group, a formyl group, a $C_2$–$C_7$ acyl group, a benzoyl group optionally substituted with $C_1$–$C_6$ alkyl, a $C_2$–$C_7$ alkoxycarbonyl group, a phenoxycarbonyl group optionally substituted with $C_1$–$C_6$ alkyl, an amino group optionally substituted with $C_1$–$C_6$ alkyl, an amido group optionally substituted with $C_1$–$C_6$ alkyl, a nitro group, a sulfonyl group substituted with $C_1$–$C_6$ alkyl or a phenyl group optionally substituted with $C_1$–$C_6$ alkyl, a sulfonic ester group substituted with $C_1$–$C_6$ alkyl or a phenyl group optionally substituted with $C_1$–$C_6$ alkyl, a $C_1$–$C_6$ fluoroalkyl group or a $C_1$–$C_3$ aminoalkyl group;

m and n independently represent 1 or 2;

v represents an integer 0 to 3; and

Q represents oxygen atom, sulfur atom or —NR— where R represents $C_1$–$C_6$ alkyl.

5. The process of claim 4, wherein said hydroxyl-containing lactone is δ-gluconolactone.

6. A phosphine ligand-palladium complex prepared from the triphenylphosphine derivative of claim 1 and at least one palladium compound selected from the group consisting of palladium benzylideneacetones, palladium acetylacetonates, nitrile palladium halides, olefin palladium halides, palladium halides and palladium carboxylates.

7. A phosphine ligand-palladium complex prepared from the triphenylphosphine derivative of claim 2 and at least one palladium compound selected from the group consisting of palladium benzylideneacetones, palladium acetylacetonates, nitrile palladium halides, olefin palladium halides, palladium halides and palladium carboxylates.

8. A phosphine ligand-palladium complex prepared from the triphenylphosphine derivative of claim 3 and at least one palladium compound selected from the group consisting of palladium benzylideneacetones, palladium acetylacetonates, nitrile palladium halides, olefin palladium halides, palladium halides and palladium carboxylates.

9. A phosphine ligand-palladium complex prepared from the triphenylphosphine derivative of claim 1 and at least one palladium compound selected from the group consisting of bis(benzylidene)acetone palladium, palladium bisacetylacetonate, dichlorobisacetonitrile palladium, dichlorobisbenzonitrile palladium, dichloro (1,5-cyclooctadiene)palladium, bis(1,5-cyclooctadiene)palladium, tris(dibenzylideneacetone) dipalladium, palladium chloride and palladium acetate.

10. A phosphine ligand-palladium complex prepared from the triphenylphosphine derivative of claim 2 and at least one palladium compound selected from the group consisting of bis(benzylidene)acetone palladium, palladium bisacetylacetonate, dichlorobisacetonitrile palladium, dichlorobisbenzonitrile palladium, dichloro (1,5-cyclooctadiene)palladium, bis(1,5-cyclooctadiene)palladium, tris(dibenzylideneacetone) dipalladium, palladium chloride and palladium acetate.

11. A phosphine ligand-palladium complex prepared from the triphenylphosphine derivative of claim 3 and at least one palladium compound selected from the group consisting of bis(benzylidene)acetone palladium, palladium bisacetylacetonate, dichlorobisacetonitrile palladium, dichlorobisbenzonitrile palladium, dichloro (1,5-cyclooctadiene)palladium, bis(1,5-cyclooctadiene)palladium, tris(dibenzylideneacetone) dipalladium, palladium chloride and palladium acetate.

12. A phosphine ligand-palladium complex prepared from the triphenylphosphine derivative of claim 2 and dichloro(1,5-cyclooctadiene) palladium.

13. A phosphine ligand-palladium complex prepared from the triphenylphosphine derivative of claim 3 and dichloro(1,5-cyclooctadiene) palladium.

14. A phosphine ligand-nickel complex prepared from the triphenylphosphine derivative of claim 2 and at least one nickel salt selected from the group consisting of nickel halides, nickel nitrates, nickel sulfates, nickel organocarboxylates, nickel-acetylacetonate complex salts and nickel hydroxide.

15. A phosphine ligand-nickel complex prepared from the triphenylphosphine derivative of claim 3 and at least one nickel salt selected from the group consisting of nickel halides, nickel nitrates, nickel sulfates, nickel organocarboxylates, nickel-acetylacetonate complex salts and nickel hydroxide.

16. A process for preparing a biaryl compound represented by formula (VII) by:

reacting an aryl halide derivative or aryl sulfonyl derivative represented by formula (IV) with an arylboronic acid, its derivative or an arylboronic anhydride represented by formula (V) or (VI):

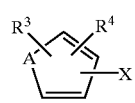

-continued

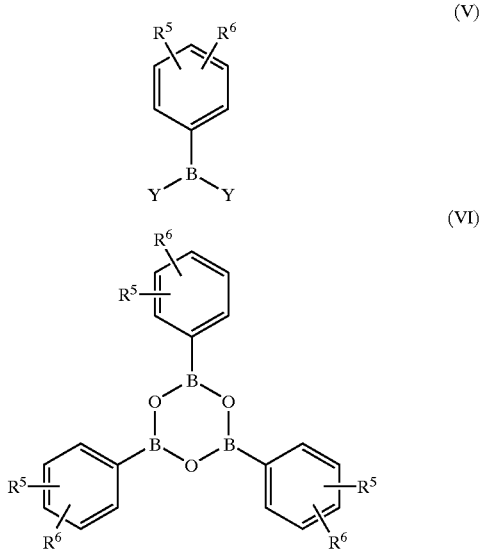

wherein in formula (IV), (V) and (VI),

A represents S, O, HC=CH or N=CH;

$R^3$, $R^4$, $R^5$ and $R^6$, which may be the same or different, each independently represent a hydrogen atom, a chlorine, a fluorine atom, $C_1$–$C_6$ alkyl group, a phenyl group optionally substituted with a $C_1$–$C_6$ alkyl, a $C_2$–$C_6$ alkenyl group, a $C_2$–$C_6$ alkynyl group, a $C_1$–$C_6$ alkoxy group, $C_1$–$C_6$ alkylthio group, a cyano group, a formyl group, a $C_2$–$C_7$ acyl group, a benzoyl group optionally substituted with $C_1$–$C_6$ alkyl, a $C_2$–$C_7$ alkoxycarbonyl group, a phenoxycarbonyl group optionally substituted with $C_1$–$C_6$ alkyl, an amino group optionally substituted with $C_1$–$C_6$ alkyl, an amido group optionally substituted with $C_1$–$C_6$ alkyl, a nitro group, a sulfonyl group substituted with $C_1$–$C_6$ alkyl substituted with a phenyl group optionally substituted with $C_1$–$C_6$ alkyl, a sulfonic ester group substituted with $C_1$–$C_6$ alkyl or substituted with a phenyl group optionally substituted by $C_1$–$C_6$ alkyl or a $C_1$–$C_6$ fluoroalkyl group;

X represents chlorine, bromine, iodine, mesylate or arenesulfonate;

Y represents a hydroxyl group, a $C_1$–$C_6$ alkoxy group, a phenoxy group optionally substituted with $C_1$–$C_6$ alkyl or a cyclohexyloxy group; or two Ys are combined together to form a group represented by formula a, b or c:

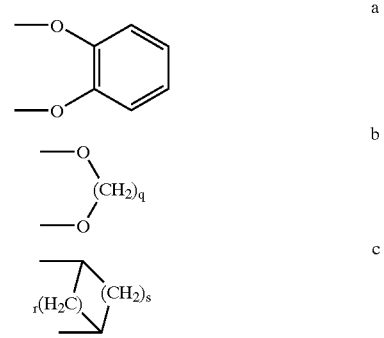

wherein q represents 1, 2, 3 or 4; and r and s each independently represent 2, 3, 4 or 5, in the presence of the phosphine ligand-palladium complex of claim 6 as a catalyst, in water, an organic solvent or a mixture of an organic solvent and water, in the presence of a base:

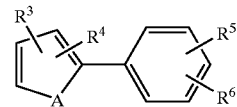

(VII)

wherein in formula (VII), A, $R^3$, $R^4$, $R^5$ and $R^6$ are as defined for formulas (IV), (V) and (VI).

17. The process of claim 16, wherein said reaction is conducted in water.

18. The process of claim 16, wherein said reaction is conducted in an organic solvent.

* * * * *